US012685604B2

(12) United States Patent
Giulianotti et al.

(10) Patent No.: US 12,685,604 B2
(45) Date of Patent: Jul. 21, 2026

(54) ROBOTIC SURGICAL STATION

(71) Applicant: THE BOARD OF TRUSTEES OF THE UNIVERSITY OF ILLINOIS, Urbana (IL)

(72) Inventors: Pier Cristoforo Giulianotti, Chicago, IL (US); Andreas Vogler, Munich (DE)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 402 days.

(21) Appl. No.: 18/253,609

(22) PCT Filed: Nov. 9, 2021

(86) PCT No.: PCT/US2021/058513
§ 371 (c)(1),
(2) Date: May 19, 2023

(87) PCT Pub. No.: WO2022/108781
PCT Pub. Date: May 27, 2022

(65) Prior Publication Data
US 2023/0414305 A1     Dec. 28, 2023

Related U.S. Application Data

(60) Provisional application No. 63/117,327, filed on Nov. 23, 2020.

(51) Int. Cl.
A61B 34/37 (2016.01)
A61B 90/50 (2016.01)
B25J 9/16 (2006.01)

(52) U.S. Cl.
CPC .............. A61B 34/37 (2016.02); A61B 90/50 (2016.02); B25J 9/1689 (2013.01)

(58) Field of Classification Search
CPC ......... A61B 34/37; A61B 90/50; A61B 50/22; A61B 34/35; A61B 34/30;
(Continued)

(56) References Cited

U.S. PATENT DOCUMENTS

| | | | | |
|---|---|---|---|---|
| 9,597,043 B1 * | 3/2017 | Mirza | .................... | A61G 13/06 |
| 2002/0039403 A1 * | 4/2002 | Oota | ...................... | A61B 6/032 378/4 |

(Continued)

FOREIGN PATENT DOCUMENTS

| | | | | |
|---|---|---|---|---|
| CN | 111658151 A | * | 9/2020 | ............. A61B 34/71 |
| DE | 102016120079 A1 | | 4/2018 | |

(Continued)

OTHER PUBLICATIONS

International Search Report and Written Opinion for Corresponding International Application No. PCT/US2021/058513, 14 pages, Apr. 21, 2022.

*Primary Examiner* — Justin C Mikowski
*Assistant Examiner* — George Samuel Gines
(74) *Attorney, Agent, or Firm* — LUCAS & MERCANTI, LLP

(57) ABSTRACT

A robotic surgical station is disclosed having a wheeled base, a partial-ring shaped structure slidably coupled to the based to be rotatable relative to the base about a horizontal roll axis passing through a center of the ring shape, a patient's bed restrained to a first arcuate segment of the partial-ring shaped structure at a first mount, a plurality of robotic arms restrained to a second arcuate segment of the partial-ring shaped structure at a second mount, and a remote control unit to command one or more of the plurality of robotic arms. The second arcuate segment is rotatable sideways with respect to the first arcuate segment to allow full access to the patient's bed by a surgeon.

22 Claims, 18 Drawing Sheets

(58) Field of Classification Search
CPC .............. A61B 2034/304; A61B 34/70; A61B
2017/3405; A61B 2034/302; A61B
2090/571; A61B 6/548; B25J 9/1689;
A61G 13/06; A61G 13/08; A61G 13/04;
A61G 7/008
USPC ....... 600/424; 5/607, 608, 610; 606/56, 251,
606/325
See application file for complete search history.

(56) References Cited

U.S. PATENT DOCUMENTS

| | | |
|---|---|---|
| 2008/0004523 A1 | 1/2008 | Jensen |
| 2016/0135905 A1 * | 5/2016 | Giulianotti ................ A61F 5/37 |
| | | 606/130 |
| 2020/0038126 A1 * | 2/2020 | Cau ........................ A61B 34/70 |
| 2020/0121267 A1 * | 4/2020 | Deutschmann ...... A61B 6/4452 |

FOREIGN PATENT DOCUMENTS

| | | | | |
|---|---|---|---|---|
| KR | 20110030038 A | * | 3/2011 | ............. A61B 34/30 |
| WO | 2014201340 A1 | | 12/2014 | |

* cited by examiner

ROBOTIC SURGICAL STATION

CROSS-REFERENCE TO RELATED APPLICATIONS

This application is a 371 of PCT/US2021/058513, filed Nov. 9, 2021, which claims the benefit of U.S. Provisional Patent Application No. 63/117,327, filed Nov. 23, 2020.

FIELD

The present disclosure generally relates to surgery robots and in particular to a robotic surgical station.

BACKGROUND

Operating rooms are currently organized mainly based on a $19^{th}$ century pre-robotic environment. With the introduction of surgical robots, particularly in the framework of laparoscopic interventions, a new era of surgery and operating room configuration has emerged.

Known robots for minimally invasive surgery—such as, for example, the "da Vinci" System®—are provided with a number of robotic arms and end effectors to which surgical tools are connected. In a typical arrangement, the robot is placed aside an operating table and remotely controlled by a surgeon, e.g. by way of special handles and pedals allowing a selective driving of the robotic arms and tools, thus carrying out a surgical intervention on a patient.

WO2014/201340A1 discloses an integrated surgical station mainly comprising a base fixed to the ground and a ring-shaped structure rotatable about a roll and a pitch axis. A patient's bed and a plurality of robotic arms are mounted onto the ring-shaped structure and movable integrally thereto.

Notwithstanding the availability of the aforementioned robotic systems and integrated robotic station, there is still a need for improved safety, versatility and mobility of the operating structures and for reducing their size and complexity without affecting reliability and quality of the surgical intervention.

SUMMARY

The above needs are met by a surgical robotic station constructed in accordance with the principles of the present disclosure.

Preferred features are the object of the examples set forth in the dependent claims.

The present disclosure relates to a robotic surgical station mainly comprising a base to be rested on the ground and an arcuate, structure, such as a suitable partial-ring shaped structure, movable with respect to the base and upon which both an operating table and a plurality of robotic arms can be releasably mounted. The robotic arms are commanded by a surgeon through a remote control unit to carry out a surgical intervention on a patient.

According to the present disclosure, the partial-ring shaped structure has an operative portion, or segment, upon which the robotic arms are mounted and that can be displaced, in particular rotated, sideways, so as to free the region around the operating table in the operating room for a surgeon or medical operator to act directly upon the patient, as needed. In this way, the surgical station can be employed for both robotic and non-robotic surgery, and can also rapidly shift from one mode to the other in specific circumstances, e.g. in emergency situations.

According to a preferred embodiment, the profile of the partial-ring shaped structure defines substantially an arc of circumference covering approximately 270 degrees out of 360 degrees of a whole ring contour.

Advantageously, the partial-ring shaped structure is rotatable relative to the base about a roll axis parallel to the ground and passing through the center of the geometrical ring profile.

The partial-ring shaped structure, the operating table and/or the robotic arms—possibly through respective mounts thereof—may also be rotatable relative to the base about a pitch axis perpendicular to the roll axis and parallel to the ground in a rest condition of the partial-ring shaped structure. In particular, the pitch axis may be an axis intercepting a diameter of the geometrical ring profile.

According to an exemplary embodiment of the present disclosure, the operating table and/or the robotic arms—through respective mounts thereof—are (also) rotatable about a yaw axis perpendicular to the roll and pitch axes relative to the partial-ring shaped structure. Such (additional) degree of freedom may, for example, ease preparation of a patient for surgery or the setup of the robotic arms and related surgical tools or end effectors.

In a preferred embodiment, in a standard condition the operating table may be positioned upon said base substantially parallel to said pitch axis, i.e. extending longitudinally according to a cord of the geometrical ring profile.

Advantageously, the operating table and the robotic arms, in particular respective mounts thereof, can be arranged at opposite sides of the partial-ring shaped structure.

The operating table and/or the robotic arms may be supported upon respective mounts having a telescopic structure, thus allowing adjusting their (mutual) position.

According to an embodiment of the present disclosure, the operating table can be configured to be removably mounted on the station base. A patient can thus be arranged on the operating table and prepared for surgery before entering the operation room, wherein the table can be connected to the surgical station. Moreover, post-surgical removal of the operating table allows the patient to be comfortably returned to his/her hospital room without transferring him/her to another bed or support.

The operating table can be generally configured as a patient's bed, for example.

Preferably, the whole robotic surgical station, at its base, can be mounted upon wheels or similar displacing devices—mobilizing the station in the surgical environment or from one environment, e.g. room, to another.

According to an exemplary embodiment of the present disclosure, the robotic arms may be modular or may be assembled on the structure at different locations, so as to allow a surgeon to arrange and re-arrange them based upon the requirements of a specific surgical intervention. To this aim, a mount of the partial-ring shaped structure may comprise an annular frame.

The number of robotic arms that may be attached to said annular frame—or to an operably connected mounting structure depending upon specific embodiments that can vary (i.e. the station implements an "open platform") depending upon the specific surgical needs. Hence, different and optimized setups of the surgical station may be achieved, e.g. for prostate surgery, lung surgery and so on.

Further advantages and features of the robotic surgical station according to the present disclosure will become clear to those skilled in the art from the following detailed and non-limiting description of embodiments thereof.

BRIEF DESCRIPTION OF THE DRAWINGS

Reference will be made to the attached drawings, wherein.

DETAILED DESCRIPTION

Figure 1:
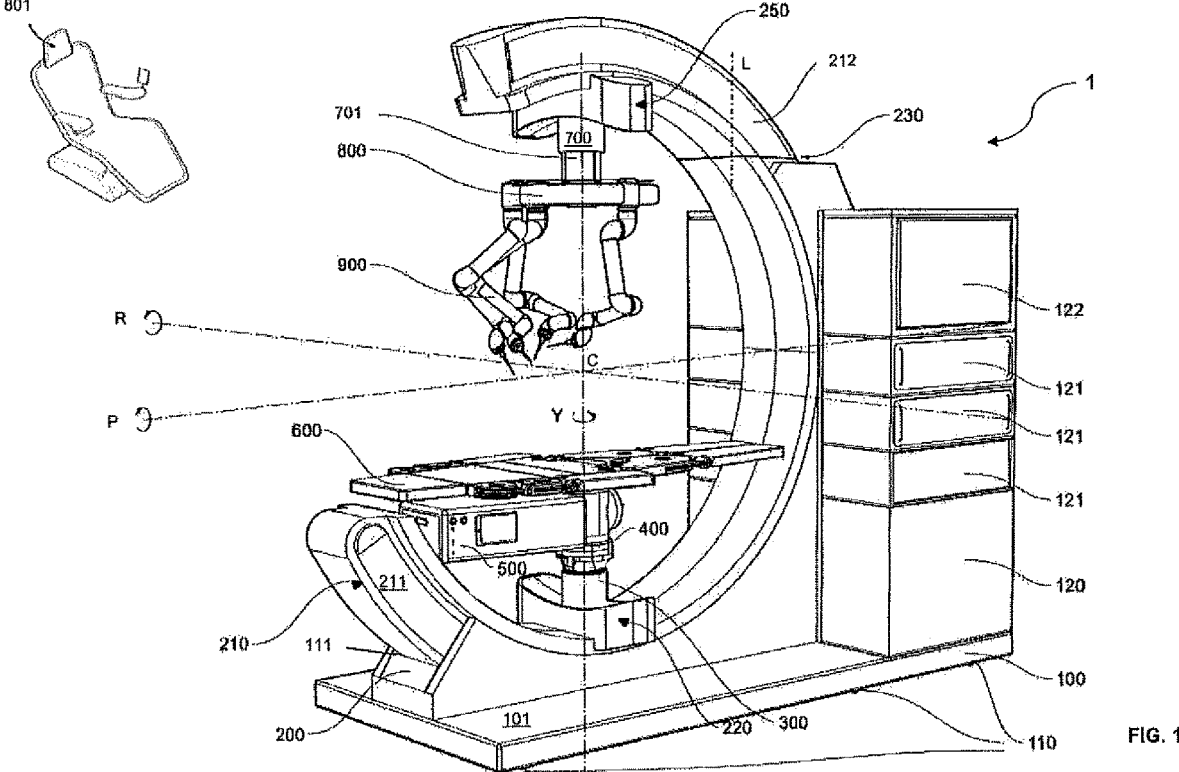
FIG. 1 shows a perspective view of an embodiment of a robotic surgical station according to the present disclosure, wherein a partial-ring shaped structure is in a default, or rest, configuration with a patient's bed substantially parallel to the ground.
Figure 2:
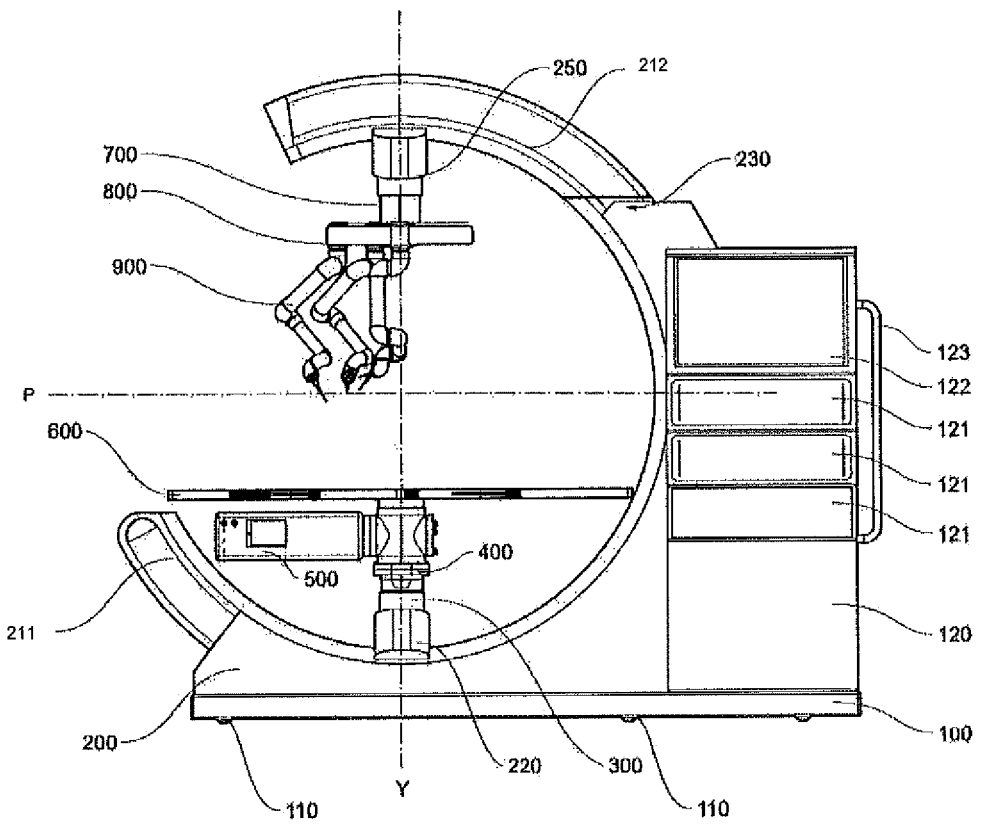
FIGS. 2 to 5 show a side view, a top view, a front view and a rear view, respectively, of the robotic surgical station of FIG. 1.
Figure 3:
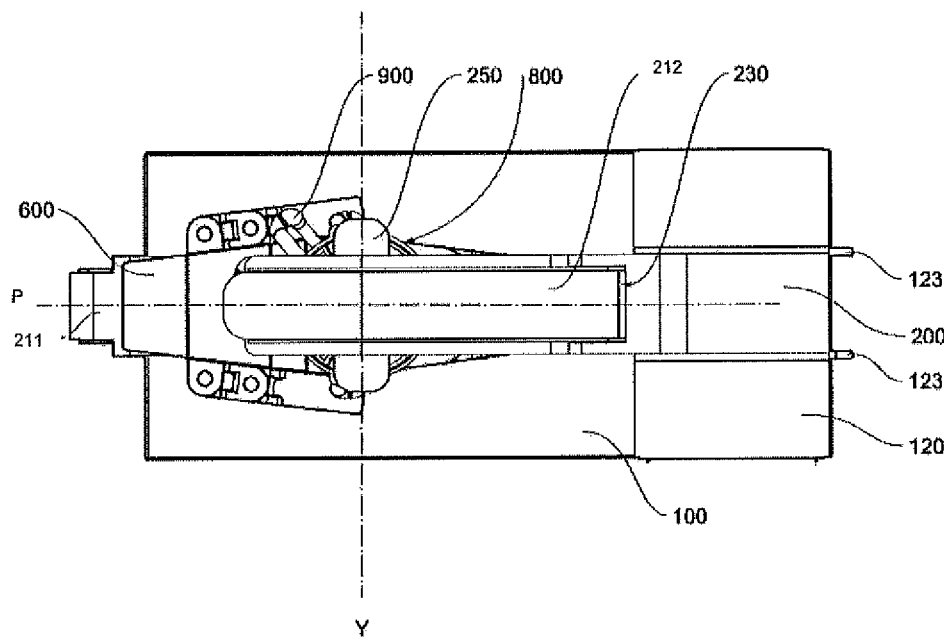
Figure 4:
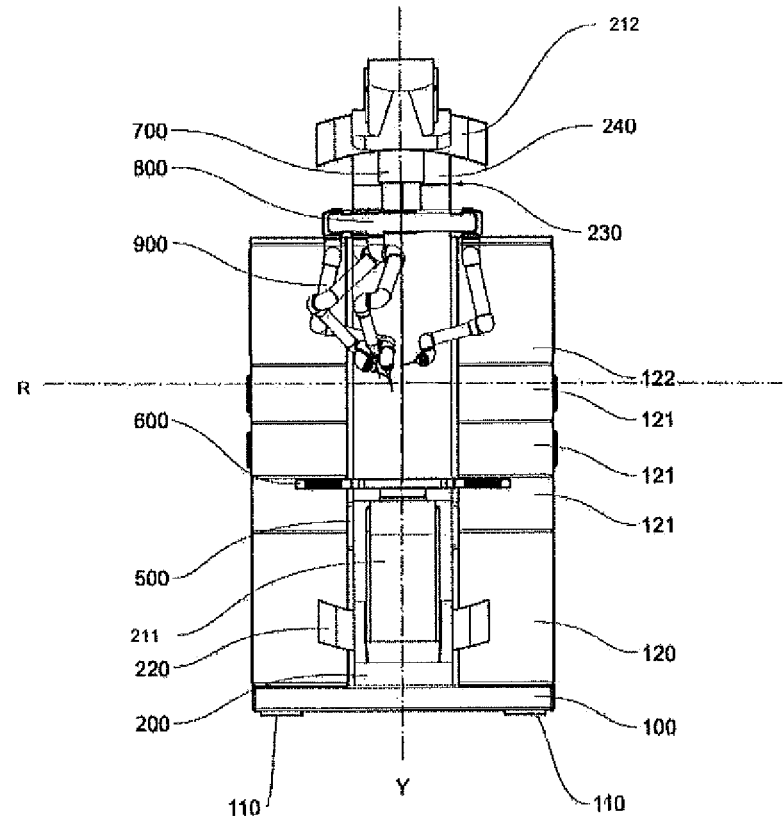
Figure 5:
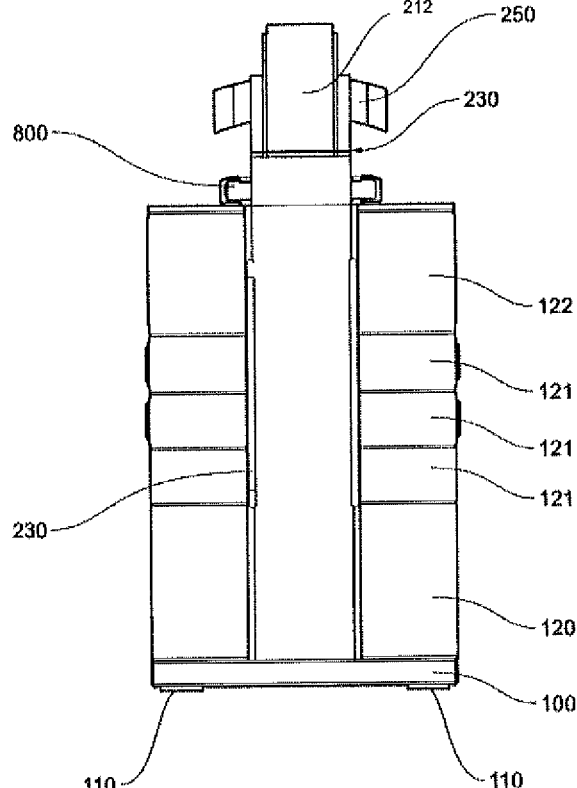

Several embodiments and variants of the robotic surgical station and its elements are set forth herein, although other embodiments are contemplated as well.

The different embodiments and variants can be used in combination, when compatible.

With initial reference to FIGS. 1 to 5, a robotic surgical station according to an exemplary embodiment of the present disclosure is set forth generally at 1. The robotic surgical station 1 can comprise a base 100, configured to be selectively rested on the ground, and a table and surgical instrument frame or structure, such as a partial-ring shaped structure 210 to which a patient's bed 600 and a plurality of robotic arms 900 can be selectively restrained, if desired and operably connected.

The robotic surgical station 1 can further comprise a remote control unit 801, represented schematically in FIG. 1, that may be used by a surgeon to carry out a surgical intervention upon a patient by actuating the partial-ring shaped structure 210, the patient's bed 600 and/or the robotic arms 900, according to the exemplary modes that will be described below.

The base 100 can be advantageously mounted upon a suitable movable support, such as wheels 110, so as to be displaceable from one environment to another. The wheels 110 can be provided with a locking system configured to avoid any undesirable movement, e.g. during a surgical intervention, or can be retracted, if desired, by the remote control unit 801 or otherwise secured to prevent rolling of the base 100 during operation of the system.

The base 100 can include a ground platform 101 that can be directly mounted upon the wheels 110 and a rack assembly 120 for integration of medical equipment for a particular procedure including, e.g., anesthesia equipment or other devices and supplies. In particular, the rack assembly 120 may be associated with rack inserts 121, a monitor 122 and handrails 123. The base 100 can also comprise a coupling element 200 fixed with the ground platform 101 and configured for receiving the partial-ring shaped structure 210 in a sliding manner, so that the latter can rotate about a roll axis R. In particular, the coupling element 200 can define an arcuate guiding seat 111 reproducing the external profile of the partial-ring shaped structure 210, so that the latter can be slidably received therein according to a circumferential trajectory of movement.

As shown in FIG. 1, the roll axis R can be horizontal and arranged perpendicularly to the geometrical ring, or circumferential, profile of the partial-ring shaped structure 210 by passing through the geometrical center C of such profile.

Rotated configurations of the partial-ring shaped structure 210 and an exemplary mechanism or system allowing such rotary movement will be described shortly with reference to FIGS. 6 to 8.

Perpendicularly to the roll axis R, still on a horizontal plane in the configuration of FIG. 1, a pitch axis P is defined, which intercepts a diameter of said geometrical profile. A yaw axis Y, perpendicular to the ground, i.e. vertical, is also represented in FIG. 1 and defines, together with the roll axis R and the pitch axis P, a Cartesian reference system that can advantageously be regarded as fixed with the partial-ring shaped structure 210 and/or with movable components of the robotic surgical station 1. In FIG. 1, the roll and pitch axis R and P define a horizontal plane and the yaw axis Y is arranged vertically. This positioning corresponds to a default, or rest, configuration of the robotic surgical station 1.

In preferred embodiments, the patient's bed 600 and/or the robotic arms 900 are rotatable about the pitch and the yaw axis P and Y. Rotated configurations of these components about such axes and exemplary mechanisms or systems allowing such movement(s) will be described shortly with reference to FIGS. 9 to 13.

As mentioned so far, the structure 210 has a partial-ring shape, in particular defining an arcuate profile shaped substantially as an arc of circumference and centered in C. In the present example, the arc of circumference covers 270 deg out of 360 deg of the whole ring/circumferential profile.

The partial-ring shaped structure 210 is made of a first, or lower, arcuate segment or portion 211 and of a second, or upper, arcuate segment or portion 212. The upper segment 212, which can also be denoted as operative segment, is restrained to the robotic arms 900 and the lower segment 211 is restrained to the patient's bed 600. The upper segment 212 is movable, in particular rotatable, with respect to the lower segment 211. Specifically, the upper segment 211 can be moved sideways, in particular rotated according to a longitudinal axis L parallel to the yaw axis Y. Displaced configurations of said operative segment 212 and an exemplary mechanism or system allowing such movement will be described shortly with reference to FIGS. 14 to 17.

Still referring to FIG. 1, the partial-ring shaped structure 210 is provided with a first mount, globally denoted by 220, configured to support the patient's bed 600 and with a second mount, globally denoted by 250, including an annular frame 800 configured for the assembly of the robotic arms 900. In the present embodiment, the first and second mounts 220, 250 are arranged opposite to each other along a diameter of the partial-ring shaped structure 210.

Preferably, in a rest configuration the patient's bed 600 is arranged by the mount 220 parallel to the pitch axis P and in any case according to a cord of the ring profile.

In FIG. 1, the first and second mounts 220, 250 are shown aligned in a vertical direction, i.e. with longitudinal axes thereof substantially perpendicular to the ground. As mentioned above, this configuration defines a default, or rest, condition for the robotic surgical station 1, wherein also the patient's bed 600 is substantially parallel to the ground.

As said above, the partial-ring shaped structure 210 is configured to be rotatable about the roll axis R, in particular of 360 deg or more, preferably both counterclockwise and clockwise.

Due to the above-described configuration of the robotic surgical station 1, the rotation of the partial-ring shaped structure 210 simultaneously determines a rotation of both the patient's bed 600 assembled on the first mount 220 and of the robotic arms 900 restrained to the second mount 800. In other words, the robotic arms 900 may be moved in mechanical synchronization with the patient's bed 600, because they are mounted on the same partial-ring shaped structure 210. Therefore, the patient's bed 600 and the robotic arms 900 may maintain their initial mutual positioning setup during the whole surgical intervention, if the latter so requires.

Figure 6:
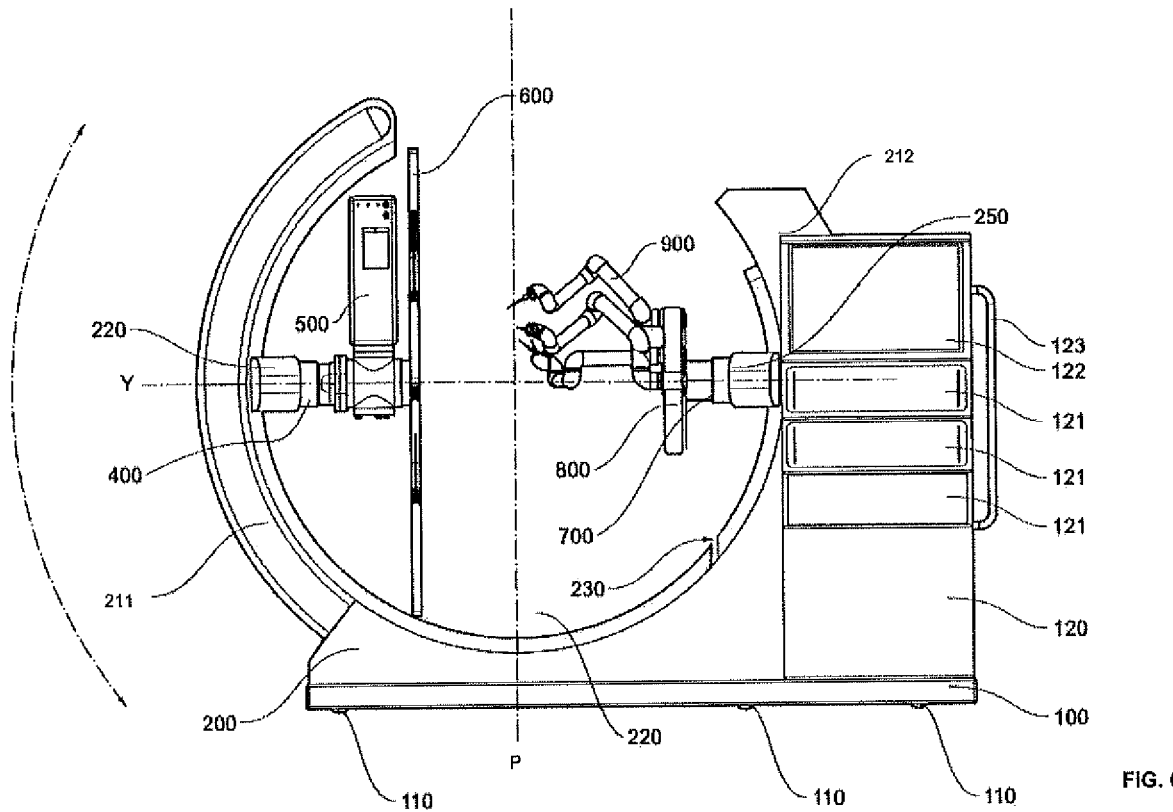
FIG. 6 shows a side view of the robotic surgical station of FIG. 1, wherein the partial-ring shaped structure is rotated by 90° clockwise about a roll axis thereof.

As shown in FIG. 6, the partial-ring shaped structure 210 may e.g. be rotated by 90 deg counterclockwise about the roll axis R so as to move the patient's bed 600 from a first position substantially parallel to the ground as in FIG. 1—corresponding to a traditional resting position of a surgical table—to a second position substantially perpendicular to the ground, which is often used in laparoscopic surgery to exploit gravity as a means to move the internal organs of a patient in order to create room for a better maneuvering of surgical instruments.

Figure 7:
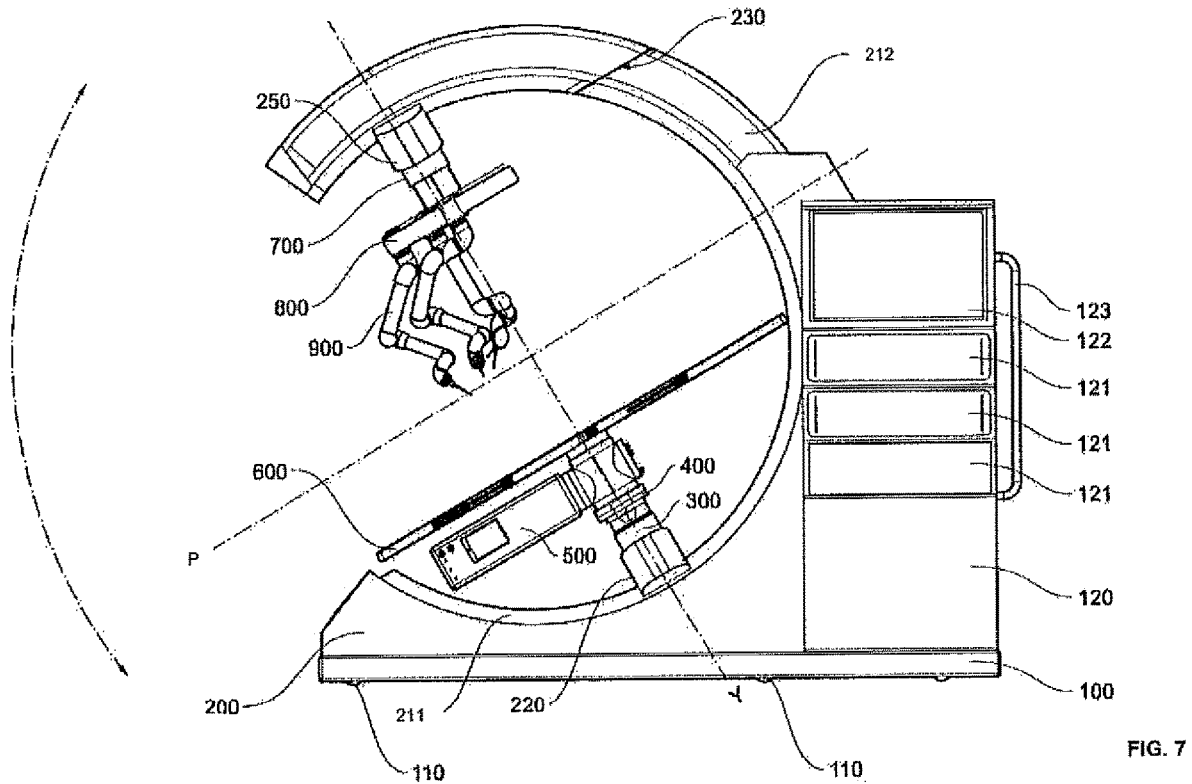
FIG. 7 shows a side view of the robotic surgical station of FIG. 1, wherein the partial-ring shaped structure is rotated counterclockwise about a roll axis thereof.

Similarly, as shown in FIG. 7, the partial-ring shaped structure 210 can be rotated clockwise to bring the patient's bed 600 at an inclination needed for a specific surgical need. Preferably, backward range of rotation allowed is of at least 30 deg.

Figure 8:
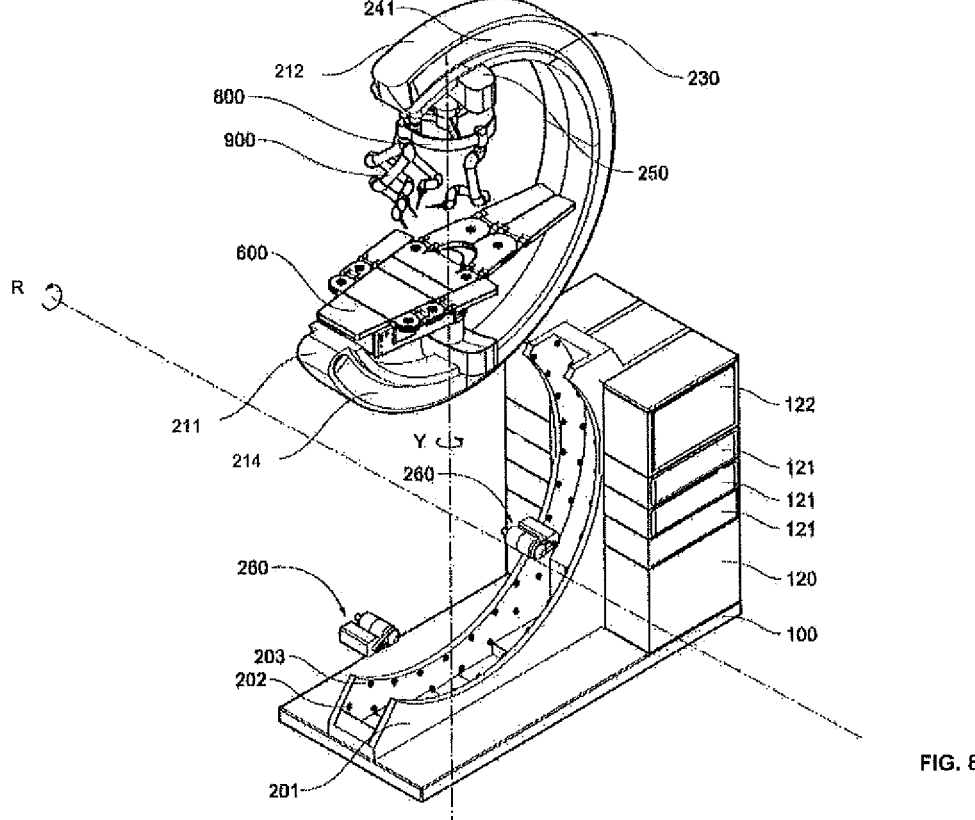
FIG. 8 shows a perspective, partially exploded view of the robotic surgical station of FIG. 1, wherein an example of a system for rotating the partial-ring shaped structure according to a roll axis is visible.

According to an embodiment of the present disclosure, rotation of the partial-ring shaped structure 210 about the roll axis R may be obtained by way of a system exemplified in FIG. 8.

In particular, the partial-ring-shaped structure 210 is rotated about the roll axis R by guide rails 214 obtained on a lateral surface of the lower portion 211 and by guide rails 241 obtained on a lateral surface of the upper portion 212.

These guide rails cooperate with guide rolls 202 and 203 respectively. The rolls are mounted on a guide conduct frame 201 of coupling element 200. The movement is actuated, e.g., by two motor/gear units 260.

As mentioned above, according to a preferred embodiment of the present disclosure the patient's bed 600 and the robotic arms 900, through part of their respective mounts 220 and 250, are also rotatable about the pitch axis P.

Figure 9:
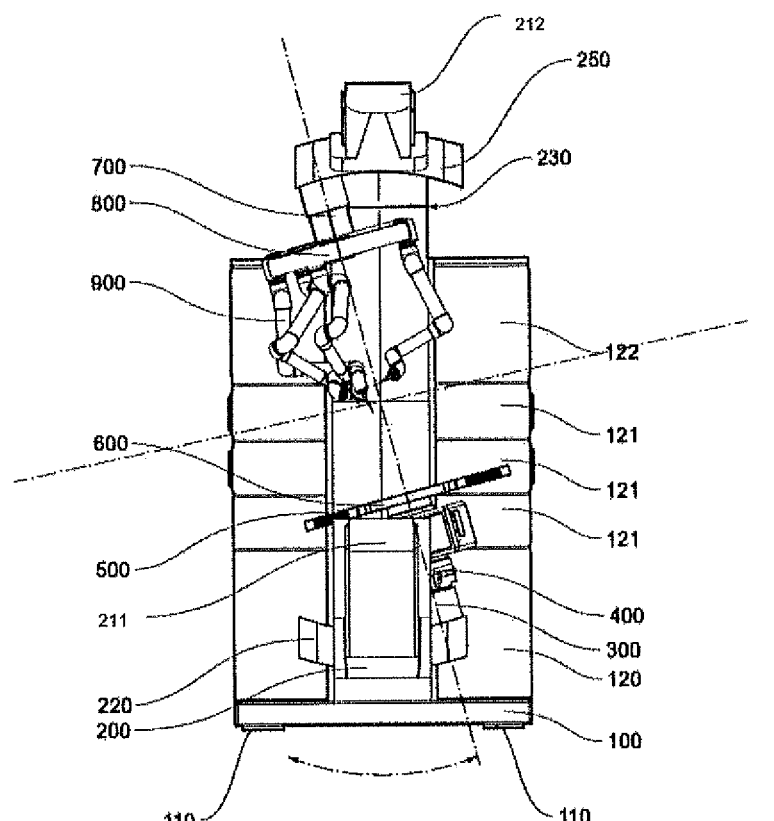
FIGS. 9 and 10 show each a front view of the robotic surgical station of FIG. 1, wherein the partial-ring shaped structure is rotated counterclockwise and clockwise, respectively, about a pitch axis thereof.
Figure 10:
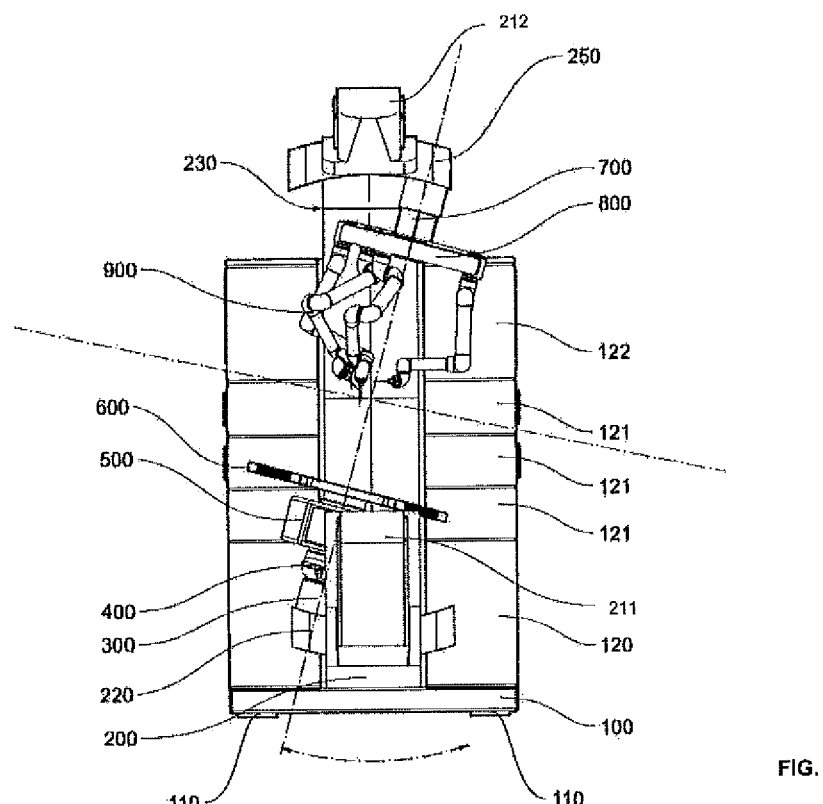

FIGS. 9 and 10 schematically show how the above components may be rotated clockwise or counterclockwise about the pitch axis P.

The rotation of the about the pitch axis P of the patient's bed 600 and the robotic arms 900 is electro-mechanically synchronized.

Figure 11:
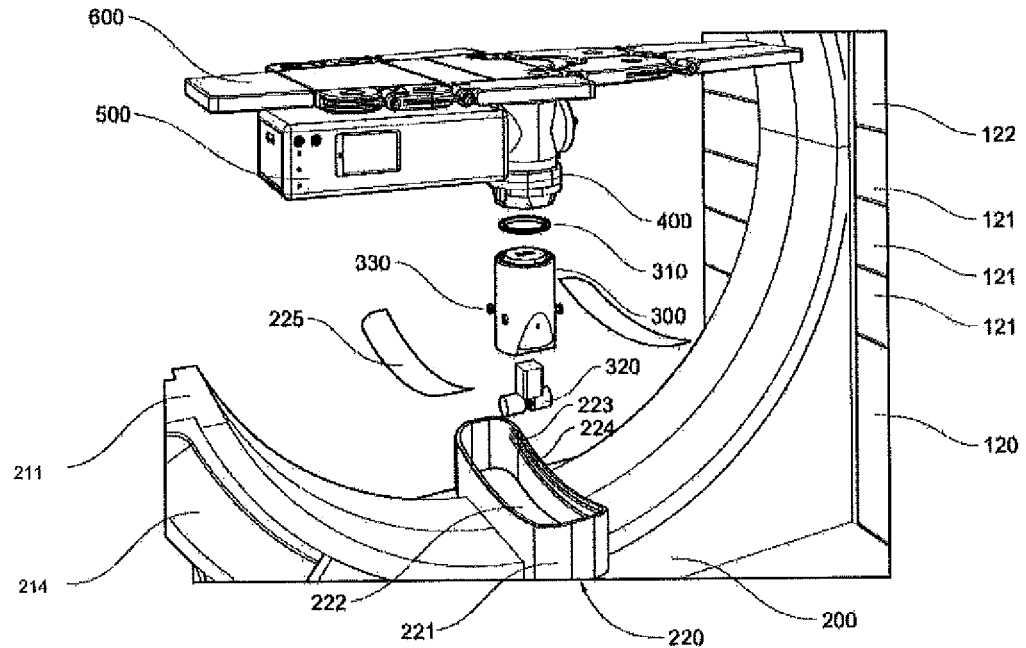
FIG. 11 shows a perspective, partially exploded view of part of the robotic surgical station of FIG. 1, wherein an example of a system for rotating a patient's bed according to a pitch and a yaw axis is visible.

According to an embodiment of the present disclosure, the above rotation about the pitch axis P of the patient's bed 600 may be obtained by way of a system exemplified in FIG. 11. The same or a similar system may be employed for the mount 250 of the robotic arms 900.

The range of rotation can advantageously be of +1-15 degrees, preferably +/−12 deg.

The mount 220 has an arcuate profile element, preferably developing about the pitch axis P or an axis parallel thereto. The mount 220 comprises a shroud 221, a gear or friction rim 222, a lower guide rail 223 and an upper guide rail 224 for the mechanical definition of the movement around the pitch axis P. A flexible protection cover 225 is protecting the mechanism. The guide rails 223 and 224 cooperate with guide rolls 330 mounted on telescopic support, or outer cylinder, 300 for the patient's bed 600. The movement is actuated, in the present example, by a motor gear assembly 320. All ball-bearing 310 allows a movement of the patient's bed 600 along the yaw axis Y, as explained also below.

Thanks to this configuration of the robotic surgical station 1 according to an embodiment of the present disclosure, the patient's bed 600 and the robotic arms 900 may simultaneously be rotated about two horizontal axes, namely the roll axis R and the pitch axis P, while maintaining their initial mutual positioning setup. This allows a surgeon to move the patient relative to the ground according to two rotational degrees of freedom.

With reference also to FIG. 1, according to an embodiment of the present disclosure the first and second mounts 220, 250 may advantageously have a telescopic structure along the yaw axis Y, so as to allow adjusting the relative distance between the patient's bed 600 and the robotic arms 900, for example during an initial setup phase. In the present embodiment, thus, the first and second mount can be moved telescopically along the yaw axis Y.

In particular, the first mount 220 implements a substantially T-shaped connector to the partial-ring shaped structure 210. It includes a telescopic structure comprising the aforementioned outer cylinder 300 and an inner cylinder 400 slidably fitted in the outer cylinder 300. The free end of the inner cylinder 400 comprises a flange upon which the patient's bed 600 is assembled and restrained.

The first mount 220 may include a hydraulic linear actuator or an electromechanical linear actuator.

The second mount 250 has a telescopic structure comprising an outer cylinder 700 and an inner cylinder 701 slidably fitted in the outer cylinder 700. The free end of the inner cylinder 701 comprises, or is fixed to, the annular frame 800 allowing the assembly of the robotic arms 900. The annular frame 800 is restrained to the inner cylinder 701 by way, e.g., of radial members.

Similarly to the first telescopic mount 220, also the second telescopic mount 250 may be configured as a hydraulic linear actuator or as an electromechanical linear actuator.

According to an embodiment of the present disclosure, the first and second mount 220 and 250, or parts thereof, are rotatable about the yaw axis Y. To this aim, a gear motor may e.g. be arranged inside the inner cylinder 400, 701 of each mount 220, 250.

In this way, the patient's bed 600 and the robotic arms 900 may be rotated relative to the partial-ring shaped structure 210 depending upon specific needs of the surgery or of the surgeon's staff. Hence, the positioning of the patient's bed 600 and/or of the robotic arms 900 may be further optimized.

Rotations of the patient's bed 600 and of the robotic arms 900 about the yaw axis Y may be simultaneous, similarly to the other movements of the surgical station, thus allowing maintaining the mutual positioning set up.

Rotations of the patient's bed 600 and the robotic arms 900 about the yaw axis Y— and possibly also with respect to the pitch axis P—may also be not simultaneous, e.g. in order to allow to prepare the patient for surgery or to move him/her from the surgical station to a hospital bed for transportation to a hospital room.

Figure 12:
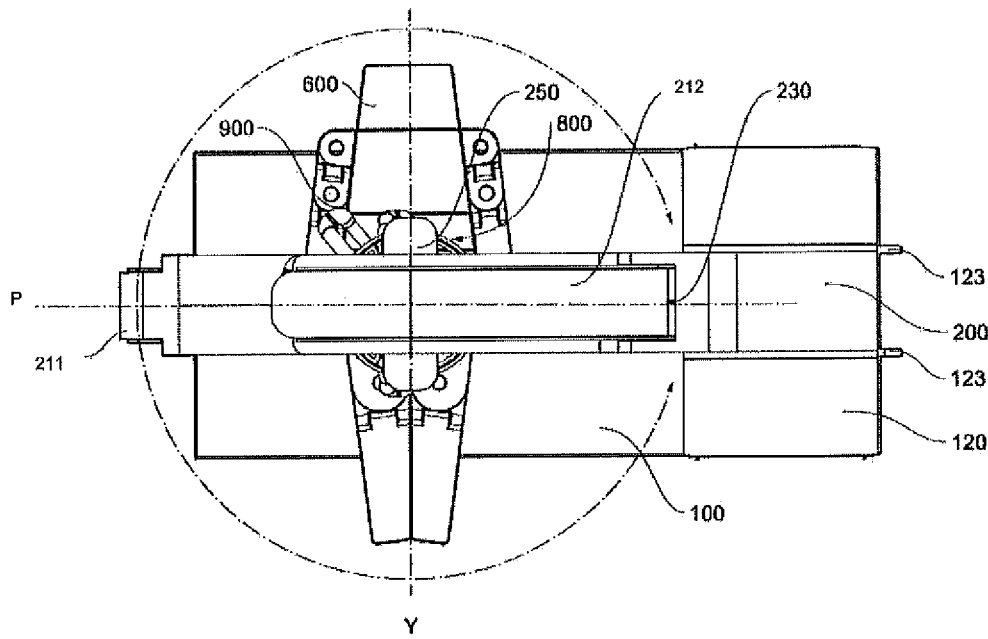
FIGS. 12 and 13 show a top and a front view, respectively, of the robotic surgical station of FIG. 1, wherein the patient's bed is rotatable by 90 degrees about a yaw axis.
Figure 13:
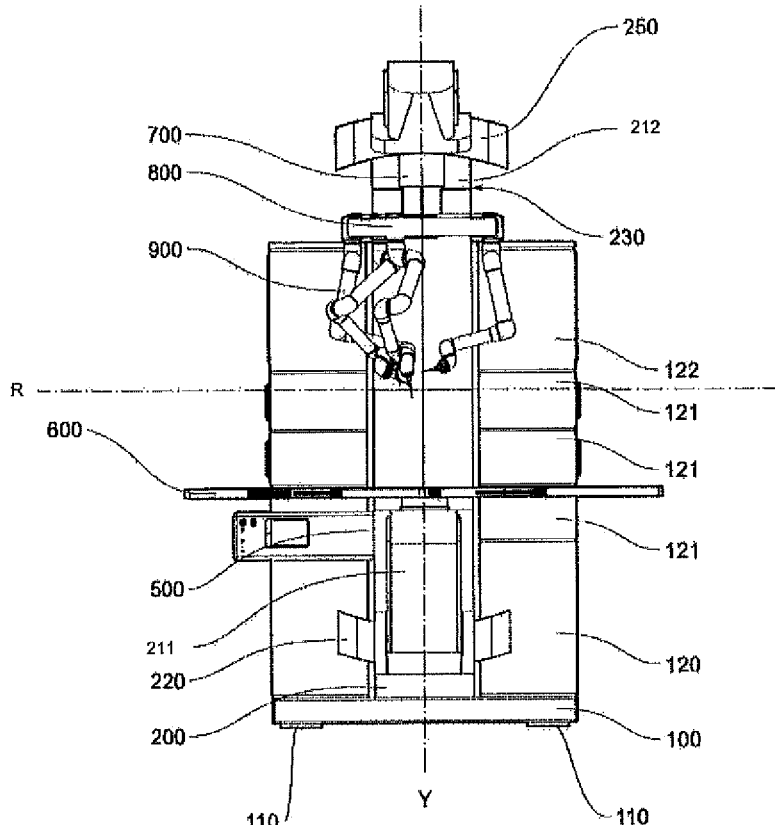

FIGS. 12 and 13 show a rotated configuration of the patient's bed 600 of 90 deg about the yaw axis Y.

Figure 14:
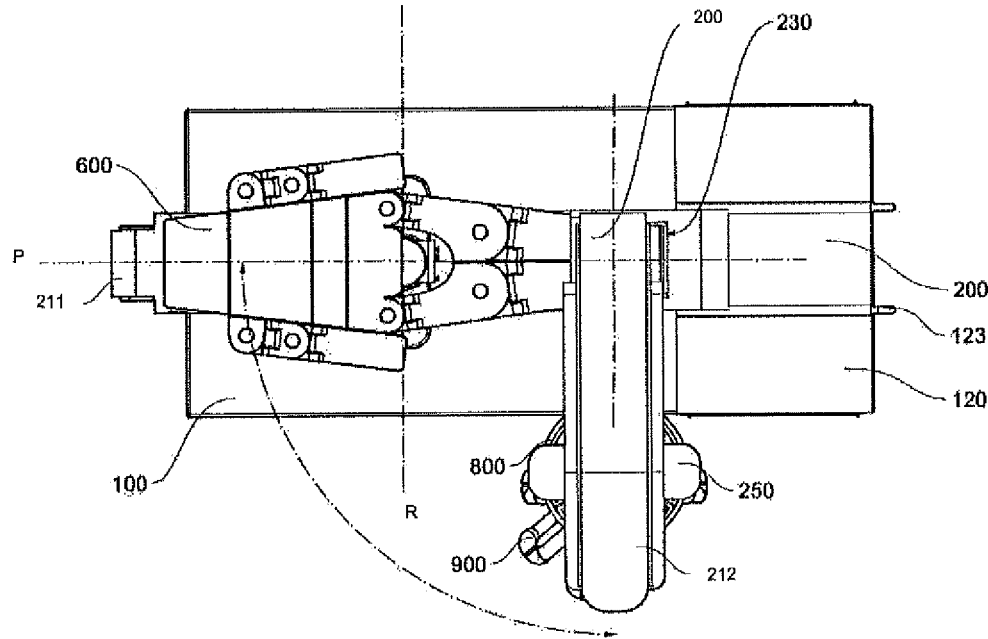
FIG. 14 shows a top view of the robotic surgical station of FIG. 1, wherein an operative segment of the partial-ring shaped structure is rotatable sideways, in particular clockwise, about a yaw axis thereof.
Figure 15:
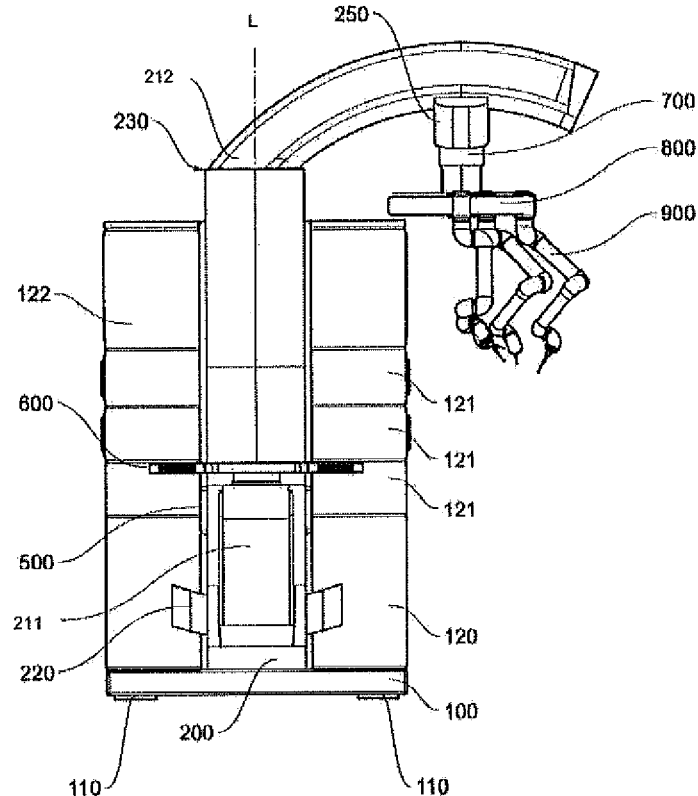
FIG. 15 shows a front view of the robotic surgical station of FIG. 1, wherein an operative segment of the partial-ring shaped structure is rotatable sideways, in particular counterclockwise, about a yaw axis thereof.

FIGS. 14 and 15 show possible configurations associated with rotation of the operative segment 212 of the partial-ring shaped structure 210 about axis L.

Figure 16:
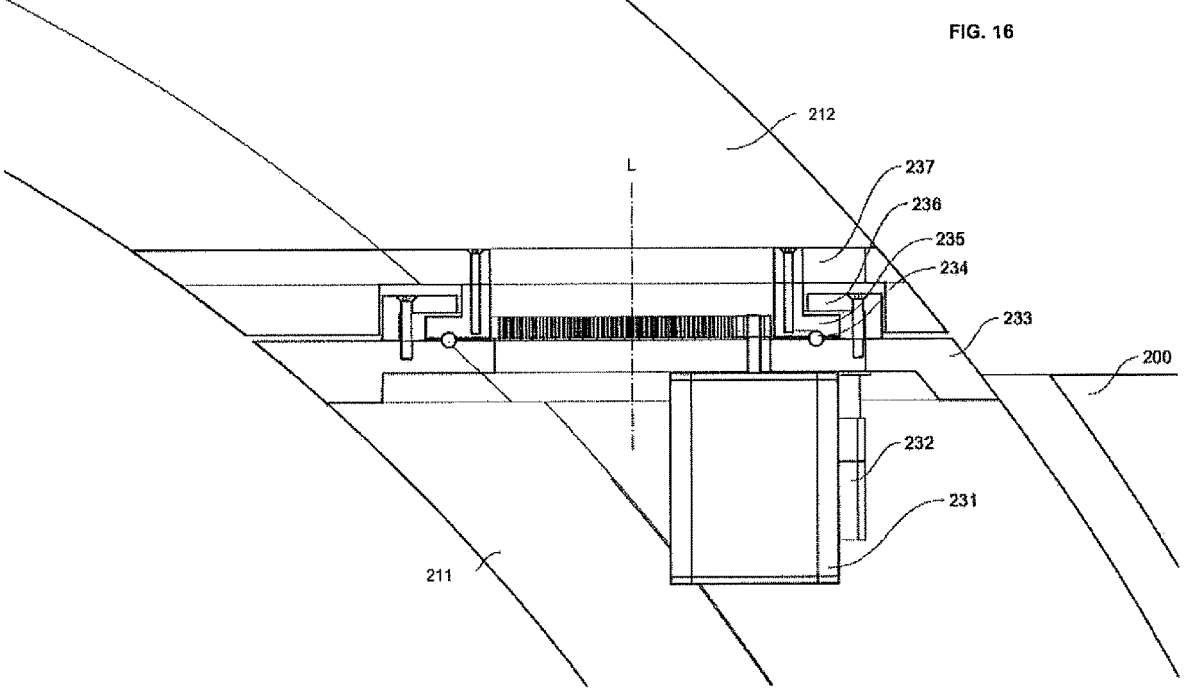
FIGS. 16 and 17 show a partially sectional view according to a vertical plane and a partially exploded view, respectively, of the partial-ring shaped structure of the robotic surgical station of FIG. 1, wherein an example of a displacing system of an operative segment thereof is visible.
Figure 17:
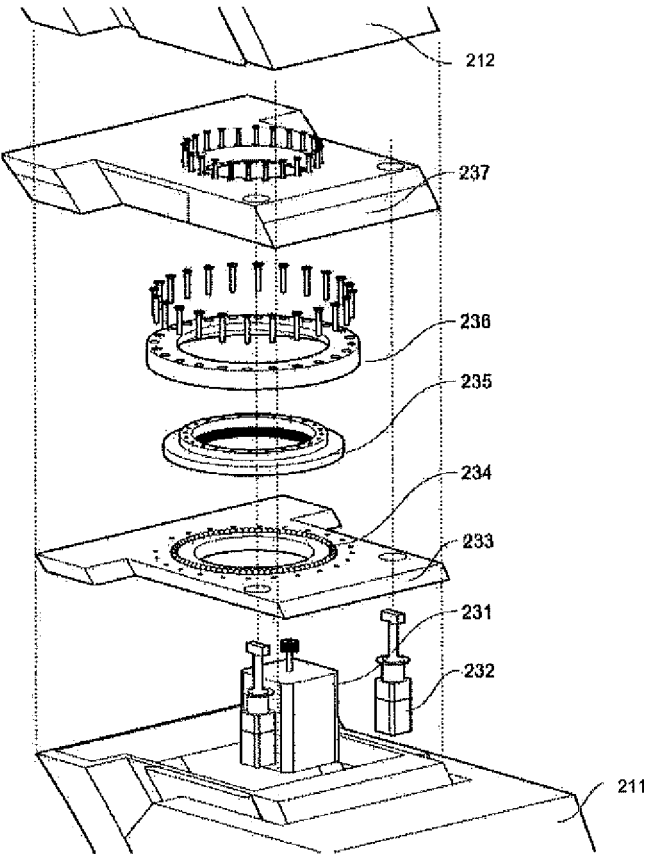

FIGS. 16 and 17 show a cross-section and an exploded view, respectively, of a rotation mechanism 230 allowing to turn the upper segment 212 sideways to allow, e.g., the preparation of the robotic arm for surgery or the free access to the patient for non-robotic surgery.

The mechanism 230 comprises a base plate 233, which is mounted, in particular fixed, on the lower segment 211 of the partial-ring shaped structure 210. The base plate 233 holds a ball-bearing 234. On the ball-bearing 234 a rotation ring 235 with an internal sprocket is mounted by a fixing ring 236. On the rotation ring 235 a top plate 237 is fixed with screws. The top plate 237 is mounted onto the upper part 212 of the partial-ring shaped structure 210. A gear motor 231 allows the supported rotation of the upper segment 212. In a non-rotated position, the upper part 212 of the partial-ring shaped structure 210 is fixed to the lower part 211 by two electromechanical or hydraulic clamping elements 232, or locking actuators.

Thanks to the overall configuration as disclosed above, the surgical station 1 may have three rotational degrees of freedom, i.e. rotation about roll, pitch and jaw axis.

According to an embodiment of the present disclosure, the patient's bed 600 may advantageously be configured to be removably mounted on the first mount 220.

Below the patient's bed 600 a control panel and/or a medicament closet 500 can be provided, e.g. for receiving inputs by an operator during surgery or in the set-up phase.

According to a preferred embodiment of the present disclosure, the annular frame 800 is configured to allow assembly of the robotic arms 900 at different operating positions.

In its more general definition, the present disclosure also relates to the combination of the base 100 with the partial-ring shaped structure 210, wherein the patient's bed 600, the robotic arms 900 and possibly their respective mounts and mounting components are provided separately and/or at a later stage of assembly or manufacturing.

Figure 18:
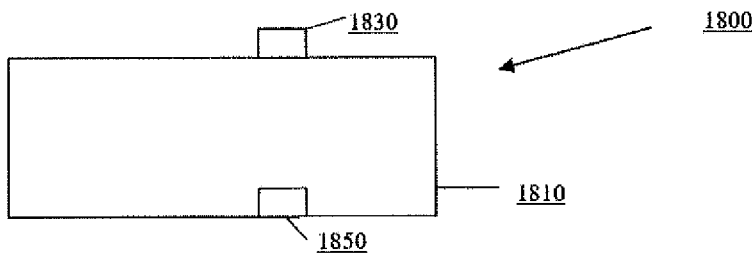
FIG. 18 illustrates an exemplary robotic surgical station configured to provide mobility and operating table accessibility, in accordance with the principles herein.

In another embodiment illustrated in FIG. 18, a robotic surgical station shown generally at 1800, can be configured such that rotation of the structure 1810 simultaneously can determine a rotation of both the patient's bed 1820 assembled on the first mount 1830 and of the robotic arms 1840 restrained to the second mount 1850. In other words, movement of the robotic arms 1840 can be synchronized with movement of the patient's bed 1820, since the robotic arms are mounted on the same structure 1810. Therefore, the patient's bed 1820 and the robotic arms 1840 can maintain their initial position relative to one another while undergoing synchronized repositioning, if desired.

Further, both the patient's bed and the robotic arms, through mounts 1830 and 1850, respectively, can be rotatable about a pitch axis P, both clockwise and counterclockwise, such that a number of surgical positions are achievable in accordance with the principles herein.

It is understood that the foregoing detailed description is merely illustrative and is not to be taken as a limitation of the scope of an embodiment of the present disclosure, which is defined solely by the appended claims and their equivalents. Various changes and modifications to the disclosed embodiments will be apparent to those skilled in the art.

| EXEMPLARY COMPONENTS' LIST | | | |
|---|---|---|---|
| 1 | robotic surgical station | 300 | outer cylinder (of 220) |
| 100 | base | 400 | inner cylinder (of 220) |
| 101 | ground platform | 700 | outer cylinder (of 250) |
| 120 | rack assembly | 701 | inner cylinder (of 250) |
| 121 | rack inserts | 230 | rotation mechanism |
| 122 | monitor | | about L |
| 110 | wheels | 233 | base plate (of 230) |
| 200 | coupling element | 234 | ball-bearing (of 230) |
| 111 | guiding seat | 235 | rotation ring (of 230) |
| 600 | patient's bed | 236 | fixing ring (of 230) |
| 900 | robotic arms | 237 | top plate (of 230) |
| 801 | remote control unit | 231 | gear motor (of 230) |
| 210 | partial-ring shaped structure | 232 | clamping elements |
| 211 | lower segment | R | roll axis |
| 212 | upper segment | P | pitch axis |
| 220 | first mount (patient's bed) | Y | yaw axis |
| 250 | second mount (robotic arms) | C | geometrical center of |
| 800 | annular frame | | ring profile |
| 214, 241 | guide rails (of 210) | L | longitudinal axis |
| 202, 203 | guide rolls | | |
| 201 | guide conduct frame (of 200) | | |
| 260 | motor/gear units | | |
| 221 | shroud (of 220) | | |
| 222 | gear or friction rim (of 220) | | |
| 223, 224 | guide rails (of 220) | | |
| 330 | guide rolls (of 220) | | |
| 225 | protection cover (of 220) | | |
| 320 | motor gear assembly (of 220) | | |
| 310 | ball bearing (of 220) | | |

The invention claimed is:

1. A robotic surgical station, comprising:

a base, configured to be rested on the ground;

a partial-ring shaped structure, slidably coupled to said base so as to be rotatable about a roll axis (R) orthogonal to a circumferential profile defined by said partial-ring shaped structure and passing through a center (C) of said circumferential profile;

an operating table, restrained to a first arcuate segment of said partial ring-shaped structure at a first mount; and a plurality of robotic arms, restrained to a second arcuate segment of said partial-ring shaped structure at a second mount and configured to be remotely actuated by a surgeon,

wherein said second arcuate segment of said partial-ring shaped structure is movable sideways with respect to said first arcuate segment to allow access to the operating table.

2. The robotic surgical station according to claim 1, wherein said partial-ring shaped structure has an arcuate profile shaped substantially as an arc of circumference, covering 270 degrees out of 360 degrees of a whole circumferential profile.

3. The robotic surgical station according to claim 1, wherein said second arcuate segment of said partial-ring shaped structure is rotatable sideways about a longitudinal axis (L) orthogonal to said roll axis (R) with respect to said first arcuate segment.

4. The robotic surgical station according to claim 1, further comprising one or more locking actuators interposed between said first and second arcuate segment of said partial-ring shaped structure.

5. The robotic surgical station according to claim 1, wherein said partial-ring shaped structure has a range of rotation of 360 degrees about said roll axis (R).

6. The robotic surgical station according to claim 1, wherein said partial-ring shaped structure is rotatable about said roll axis (R) both counterclockwise and clockwise with respect to said base.

7. The robotic surgical station according to claim 1, wherein said base comprises displacing means so as to be mobile in an environment.

8. The robotic surgical station according to claim 7, wherein the base comprises a ground platform mounted upon said displacing means.

9. The robotic surgical station according to claim 1, wherein said first and/or second mount are rotatable relative to said base about a pitch axis (P) perpendicular to said roll axis (R).

10. The robotic surgical station according to claim 9, wherein rotation of said first mount and of said second mount about the pitch axis (P) is electro-mechanically synchronized.

11. The robotic surgical station according to claim 9, wherein said roll axis (R) and said pitch (P) axis are parallel to the ground in a rest configuration of the robotic surgical station.

12. The robotic surgical station according to claim 1, wherein said first and/or second mount have a telescopic structure.

13. The robotic surgical station according claim 1, wherein said first and/or second mount comprise hydraulic or electromechanic linear actuators.

14. The robotic surgical station according to claim 1, wherein said first and/or second mount, or parts thereof, are rotatable about a yaw axis (Y) perpendicular said roll (R) axis and configured to be perpendicular to the ground in a rest condition of the robotic surgical station.

15. The robotic surgical station according to claim 1, wherein the operating table is configured to be removably mounted on said partial-ring shaped structure.

16. The robotic surgical station according to claim 1, wherein said base comprises elements for integration of medical equipment.

17. The robotic surgical station according to claim 1, further comprising a remote control unit, configured to be used by a surgeon to command one or more of said plurality of robotic arms.

18. The robotic surgical station according to claim 1, wherein said operating table and said robotic arms are arranged at opposite sides of the partial-ring shaped structure.

19. A robotic surgical station comprising:
a patient bed mount and a robotic arm mount positioned on a structure including a partial-ring shaped structure slidably coupled to a base so as to be rotatable about a roll axis (R) orthogonal to a circumferential profile defined by said partial-ring shaped structure and passing through a center (C) of said circumferential profile, the patient bed mount and the robotic arm mount being configured to provide selective rotation relative to the partial-ring shaped structure about a pitch axis P that is perpendicular to the roll axis R, horizonal in a rest position of the robotic surgical station, and intercepts a diameter of the circumferential profile.

20. The robotic surgical station of claim 19, further comprising wheels and a compact configuration.

21. The robotic surgical station of claim 19, further comprising a second robotic arm mount and an anesthesia station selectively attachable to the structure.

22. The robotic surgical station according to claim 1, wherein said second arcuate segment of said partial-ring shaped structure is movable sideways relative to said first arcuate segment of said partial-ring shaped structure so that at least a portion of said second arcuate segment of said partial-ring shaped structure is movable to a position outside of said circumferential profile.

* * * * *